Figure 1:
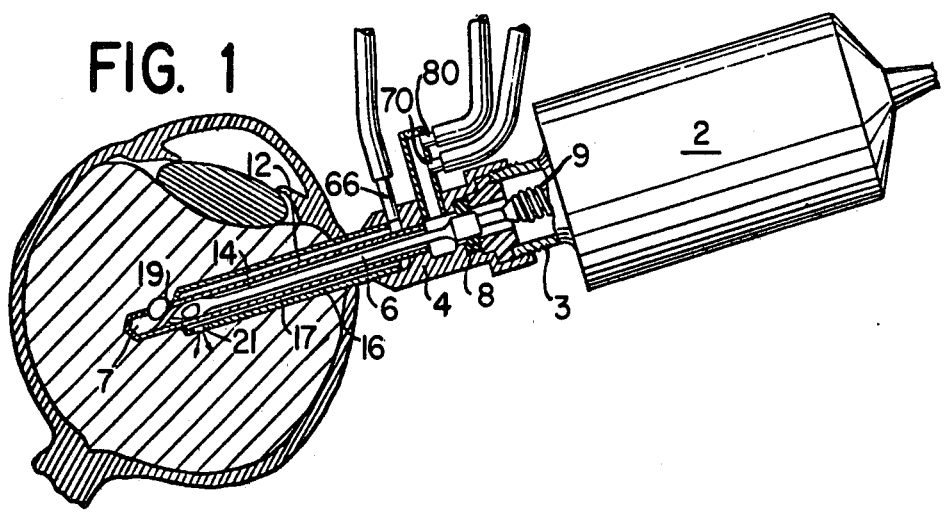

United States Patent [19]

Banko

[11] 4,436,091
[45] Mar. 13, 1984

[54] SURGICAL CUTTING INSTRUMENT WITH RELEASE MECHANISM

[75] Inventor: Anton Banko, The Bronx, N.Y.

[73] Assignee: Surgical Design Corporation, Long Island City, N.Y.

[21] Appl. No.: 245,704

[22] Filed: Mar. 20, 1981

[51] Int. Cl.³ .............................................. A61B 17/32
[52] U.S. Cl. ..................................... 128/305; 30/240; 408/6
[58] Field of Search .................... 128/305, 305.1, 755; 408/6, 9; 30/263, 240, 205, 208, 209

[56] References Cited

U.S. PATENT DOCUMENTS

| | | | |
|---|---|---|---|
| 4,167,943 | 9/1979 | Banko | 128/305 |
| 4,200,106 | 4/1980 | Douvas et al. | 128/305 |
| 4,320,761 | 3/1982 | Haddad | 128/305 |
| 4,342,528 | 8/1982 | Nozu et al. | 408/6 |

OTHER PUBLICATIONS

Kam et al., "Controlled Mechanized Trepan", Jour. of Bioeng., vol. 2, pp. 21–26, Apr. 1978.

*Primary Examiner*—Michael H. Thaler
*Attorney, Agent, or Firm*—Darby & Darby

[57] ABSTRACT

A surgical instrument including a tubular member having a port into which material to be cut is introduced there being a cutter within said tubular member having a cutting edge which is moved by a motor relative to said port to sever the material trapped between the port and the butting edge in which when the cutter movement to produce the severing movement is stopped the motor is rotated in the opposite direction to move the cutter to clear any material trapped between it and the port.

8 Claims, 2 Drawing Figures

SURGICAL CUTTING INSTRUMENT WITH RELEASE MECHANISM

Various applications exist in which instruments are used for cutting tissue. One typical application is microsurgery, for example, intraocular surgery. In such an application, tissue, bands in the vitreous portion of the eye, and other material is to be cut. Cutting can be accomplished by any of a variety of cutters, for example, the blades and jaw type cutters shown in my U.S. Pat. No. 3,732,858, granted May 15, 1973; U.S. Pat. No. 3,945,375 granted Mar. 23, 1976, U.S. Pat. No. 4,167,943, granted Sept. 18, 1979; U.S. Pat. No. 4,167,944 granted Sept. 18, 1979 and guillotine type cutters, some of which are also shown in my U.S. Pat. No. 3,844,272 granted Oct. 29, 1974 and U.S. Pat. No. 4,210,146, granted July 1, 1980, all of which are assigned to the same assignee. In the general type of cutting instrument being considered, the material to be cut is drawn into a member having a port whose surrounding surface forms a cutting surface. A cutter which has a sharp cutting edge is moved within the member having the port. The cutting action is of a shearing nature in which the cutting edge of the cutter coacts with the portion of the member surrounding the port and shears off, or severs the material between the two surfaces. In many instruments of this type, the severed material is evacuated from the operating site through the member having the port.

In such an instrument, the cutter is driven by a motor, usually an electric motor. The motor is under the control of the person using the instrument and, typically, controlled by a foot pedal switch operated by the user. The switch in turn can be connected to a control console which can control other operating features of the system with which the instrument is being used, for example, the flow of infusion fluid, the evacuation flow of the material severed by the cutter, etc.

During the typical operation, the cutting means is started and stopped a number of times to permit the surgeon to accomplish the desired result. In a typical situation, the surgeon may cut a piece of tissue or one or more bands and then stop the instrument so that he can move it to another location and begin a cutting action there. However, sometimes when the surgeon wishes to move the instrument from one place to another, material is trapped between the coating surfaces of the cutter and member having the port.

To release the material held between the coacting cutting edges when the instrument is to be moved from one location to another, it is possible to stop the motor and the cutter that it drives and to thereafter manually reverse the direction of the motor or to provide a separate position on the foot switch to accomplish this. The former procedure requires time and a separate operation on the part of the surgeon to reach over to the control console, to operate a reverse direction switch and to then energize the foot switch controlling the motor to cause it to rotate in the opposite direction. Providing an additional position on the foot switch also has a disadvantage in that it increases the complexity of the foot switch and, also, the number of positions through which the surgeon has to move it to achieve the various operating functions of the machine. In general, it has been found desirable to keep the number of positions on the foot switch to a minimum so that the surgeon will find it easy to select the correct position for the foot switch to select the desired system function.

Accordingly, the present invention is directed to an arrangement for automatically controlling the cutting mechanism of a surgical instrument. In accordance with the invention, the cutting instrument is motor-driven. When the surgeon operates the control switch to cause the motor to turn in a direction to produce the cutting action, the motor will do this. As soon as the surgeon releases the control switch to thereby stop the motor, a circuit is operated to rotate the motor in the reverse direction. This moves the active portion of the cutter away from the coacting surface of the member having the port between which the material may have been trapped thereby to release the tissue.

It is therefore an object of the present invention to provide an automatic control for the cutter element of a surgical instrument which clears material held in the cutting opening of the instrument when the drive motor for the cutting element has been stopped.

A further object is to provide an automatic control for a surgical instrument for reversing the direction of motion of the active cutting element when the instrument has been stopped.

Still a further object is to provide an automatic control for a surgical instrument in which the cutting action is carried out by moving the cutter element in a first direction relative to a cutting surface and when the cutting action is stoped, to automatically move the cutter element in a second direction to clear the cutting opening.

Figure 2:
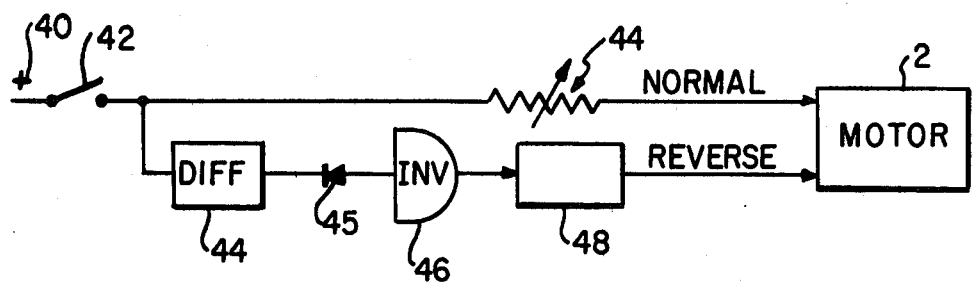

Other objects and advantages of the present invention will become more apparent upon reference to the following specification and annexed drawings in which:

FIG. 1 is an overall plan view, taken partly in crossed-section of a typical instrument for use with a system of the present invention; and FIG. 2 is a schematic diagram showing the control portion of the circuit.

FIG. 1 shows a typical surgical instrument 10 with which the system can be used. It should be understood, however, that the system can be used with most types of instrument or instrument set-ups which utilize a mechanical cutting action. This includes any of a number of various types of mechanical cutting instruments (e.g. choppers, rotating cutters, guillotine type cutters, etc.).

The illustrative embodiment of the invention being described, utilizes a rotating type cutter. The tip of instrument 10 is shown as having pierced through a section of the eye, for example after an incision has been made. The tip of the instrument is shown in the vitreous of the eye to remove tissue, bands and fluid therefrom or to treat the eye. The instrument of FIG. 1 also can be used to remove material from other parts of the eye such as the lens or iris. It should be understood that the system can be used with any compatible type of instrument to perform operations or treatment in any portion of the body of a mammal.

The instrument 10 of FIG. 1 includes an electric motor 2 of the reversible type, from which extends a collar 3. A fitting 4 is fastened onto collar 3 and concentric inner and outer tubular members 12 and 16 extend from fitting 4. Inner tube 12 defines a central passage 14 through which evacuation flow of material takes place over a line 80 which communicates with passage 14 through a coupling on fitting 4. The space between the inner and the outer tubes 12 and 16 defines a passage 17 through which infusion fluid is supplied over a line 66.

The inner, evacuation flow, tubular member 12 has an opening or port 19 at the end thereof through which the severed material is evacuated from the operation field. The infusion flow tubular member 16 has an opening 21 in its wall, spaced from opening 19 to avoid interference, through which fluid is infused into the operating field.

A shaft 6, illustratively shown as having a fluted blade-type cutter 7 at the end thereof is located in the inner passage 14. The driven end of the shaft is connected to the motor 2 and rotates in bearings 8 in the fitting 4. Shaft 6 is preferably biased by a spring 9 so that as the cutter 7 is rotated, it will coact with the surface 19a surrounding the evacuation port 19 to produce a shearing action to cut any tissue therebetween. The suface 19a of the tubular member 14 surrounding port 19 can be tapered or otherwise sharpened to improve the cutting action, like a pair of scissors.

In operation, the tip of the instrument is moved to place the cutter at the site of the material to be severed. The evacuation flow through opening 19 and passage 14 aids in drawing the material into a relationship so that it can be severed by cutter 7. The surgeon operates the motor control switch so that the cutter 7 rotates to sever the tissue. The severed material, in suspension or as part of an emulsion, is drawn up passage 14 and is removed through the evacuation flow line 80.

In a typical operation, the surgeon may wish to move the instrument to another portion of the operating site to sever or treat material there. In some cases, tissue from the first site would be trapped between the shearing surfaces of the blade 7 and the part 19a of the tubular member 14 surrounding the port 19. Therefore, as the surgeon moves the instrument, he would drag with it the trapped tissue. Sometimes, the cutter blade will quickly turn slightly or the tissue will quickly slip out of the trapping area so that it will clear and the tip of the instrument can be freely moved. Other times it will not and the material will be dragged for a distance before it is released. The latter efect is undesirable.

FIG. 2 shows an arrangement for overcoming the tapping action. Here, the motor 2 is shown illustratively as being of the DC type although it should be understood that the principles of the invention apply to any type of motor. For example, AC motors, air driven motors, etc. utilizing the appropriate circuit elements. In general, in a DC motor applying voltage in one direction through the armature will cause the motor to rotate in a first direction and by applying the operating voltage through the motor armature in the opposite direction, will cause the motor to reverse direction. Other motors operate to reverse direction with other control arrangements. In FIG. 2, the motor is shown as having two control inputs, normal direction and a reverse direction.

Voltage to the motor 2 is supplied from a source 40, which can be any conventional power supply, and through a switch 42, which as previously described, can be a foot pedal operated switch. The voltage is supplied on the normal direction line via a speed control rheostat 44 which is usually located on the operating console. By adusting the rheostat, the speed of the motor in the forward direction can be controlled.

The output side of the switch 42 is also connected to the input of a differentiation circuit 44 whose output is connected through a diode 45 and an inverter 56 to a timed switching device 48 which can be, for example, a latching type relay with a predetermined drop-out time, a one-shot multivibrator with a predetermined time constant, etc. The function of the switching device 48 is to produce an output signal for a predetermined time after it has been triggered. The output signal is supplied to the reverse inut of the motor to cause it to turn in the direction opposite to that needed for cutting.

In operation, consider that the operator has depressed the switch 42 so that the voltage is supplied from the source 40 to the normal input of the motor. The motor will turn in the operating direction and produce the cutting action between cutter 7 and surface 19a. When the operator opens the switch, there is a transition at the input of differentiating circuit 44 from a positive voltage to a negative voltage. The differentiating circuit 44 produces a negative going pulse in response to this transition. This pulse is transmitted through a properly poled diode 45 as a trigger pulse and is then inverted in an inverter 46 to operate the switching control device 48 which produces an output pulse on the reverse input to the motor for a suitable time to cause the motor to rotate in the reverse direction. This causes the cutter 7 to rotate in the opposite direction and to open up the area between the cutting surface of cutter 7 and the tube surface 19a. This frees any material that was trapped between the two surfaces.

One particular form of logic convention has been shown in FIG. 2. It should be understood that any other suitable logic convention also may be utilized, i.e. negative going logic, etc.

As indicated before, the system can be used with any type of mechanical cutter. In the case, for example, of a guillotine cutter, the motor rotates a device with a cam face having a member of sectors which have a gradual rise and a sharp fall against one end of a spring biased shaft. A cutting blade is provided at the other end of the shaft. As the cam is rotated, the shaft is alternately reciprocated forward and backward against the spring thereby producing the reciprocating motion necessary for the guillotine blade.

It is also possible to design an instrument wherein the tubular member is moved either longitudinally or rotationally instead of the cutter.

What is claimed is:

1. A surgical instrument for severing by a shearing action material located between two coacting surfaces comprising
    an elongated tubular member having a surface defining an opening into which material to be severed is introduced,
    a cutter means disposed within said tubular member and having a cutting surface to coact with the surface of said tubular member defining and opening for producing a shearing action of material between said cutting surface and said surface of said tubular member,
    means for moving one of said cutting means and tubular member to produce relative motion in a first direction to produce the shearing action of material between said coacting surfaces,
    and means responsive to the controlled stopping of relative movement in said first direction causing said moving means to produce relative motion between said cutter means and said surface of said tubular member in a second direction opposite to said first direction for a predetermined amout to clear material trapped therebetween, said cutter means always remaining within said tubular member.

2. An instrument as in claim 1 wherein said moving means moves said cutter means.

3. An instrument as in either of claims 1 or 2 wherein said moving means comprises an electric motor.

4. An instrument as in claim 1 wherein said cutting means is rotatable and said moving means is a bidirectional rotating motor, said motor being rotated in the first direction to produce said shearing action and rotated for a predetermined amount in said second direction to clear the material.

5. An instrument as in claim 4 wherein said motor is coupled to said cutter means to rotate said cutter means relative to said tubular member.

6. An instrument as in claim 1 wherein said responsive means comprises means for sensing the stopping of said moving means and means for applying a signal to said moving means to cause it to operate in a direction to produce relative motion opposite to said first direction.

7. An instrument as in claim 6 wherein said moving means comprises a motor, said responsive means including means for reversing the direction of rotation of said motor.

8. An instrument as in claim 7 wherein said motor is an electric motor, said responsive means including means for sensing a condition when power applied to rotate said motor in a first direction is removed.

* * * * *